(12) United States Patent
Aleotti et al.

(10) Patent No.: US 7,727,955 B2
(45) Date of Patent: Jun. 1, 2010

(54) PHARMACEUTICAL COMPOSITIONS BASED ON NK2 ANTAGONISTS FOR PEDIATRIC USE

(75) Inventors: Alberto Aleotti, Fiesole (IT); Maria Altamura, Florence (IT); Carlo Alberto Maggi, Florence (IT)

(73) Assignee: Laboratori Guidotti S.p.A., Pisa (IT)

( * ) Notice: Subject to any disclaimer, the term of this patent is extended or adjusted under 35 U.S.C. 154(b) by 279 days.

(21) Appl. No.: 11/666,204

(22) PCT Filed: Oct. 26, 2005

(86) PCT No.: PCT/EP2005/055575

§ 371 (c)(1),
(2), (4) Date: Apr. 23, 2007

(87) PCT Pub. No.: WO2006/045820

PCT Pub. Date: May 4, 2006

(65) Prior Publication Data

US 2008/0090795 A1    Apr. 17, 2008

(30) Foreign Application Priority Data

Oct. 27, 2004    (IT) ............................ FI2004A0221

(51) Int. Cl.
*A61K 38/00*    (2006.01)
*A61K 38/12*    (2006.01)
*A61K 31/41*    (2006.01)
*A61K 31/451*    (2006.01)
*A61K 31/4965*    (2006.01)
*A61K 31/535*    (2006.01)
*A61K 31/5377*    (2006.01)
*A61K 31/56*    (2006.01)

(52) U.S. Cl. .................. 514/9; 514/210.2; 514/212.01; 514/317; 514/320; 514/326

(58) Field of Classification Search ........................ None
See application file for complete search history.

(56) References Cited

FOREIGN PATENT DOCUMENTS

| WO | WO 9628467 | 9/1996 |
|---|---|---|
| WO | WO 0129066 A2 | 4/2001 |
| WO | WO 03037916 A2 | 5/2003 |
| WO | WO 2004037266 A1 | 5/2004 |

OTHER PUBLICATIONS

Colic from Merck Manual, pp. 1-2. Accessed Jun. 24, 2009.*
Colic from Mylicon.com, http://www.mylicon.com/why/index.jhtml?id=mylicon/cry/colic.inc, pp. 1-2. Accessed Jun. 25, 2009.*
All about Infant Gas from Mylicon.com, http://www.mylicon.com/infantgas/index.jhtml, pp. 1-2. Accessed Jun. 25, 2009.*
Colic from Bupa Health, http://hcd2.bupa.co.uk/fact_sheets/Mosby_factsheets/infant-colic.html, pp. 1-6. Accessed Jun. 24, 2009.*
Magnan et al., "Effects of Intrathecal NK-1 and NK-2 Antagonists on Xylene-induced Cystitis in Rat," Neuropeptides: Function and Pharmacology, vol. 24, p. 199-200 (1993).
Camilleri, "Management of the Irritable Bowel Syndrome," Gastroenterology 2001; 120:652-668.
Mayer et al., "Basic and Clinical Aspects of Visceral Hyperalgesia," Gastroenterology 1994; 107:271-293.
Anton et al., "Chronic low-level administration of diquat increases the nociceptive response to gastric distention in rats . . . ," Pain 92 (2001) 219-227.
McLean et al., "Effects of nematode infection on sensitivity to intestinal distension . . . ," European Journal of Pharmacology 337 (1997) 279-282.
Toulouse et al., "Role of tachykinin NK2 receptors in normal and altered rectal sensitivty in rats," British Journal of Pharmacology (2000) 129, 193-199.
Lippi et al., "Pharmacokinetics of the Bicyclic Peptide Tachykinin NK2 Receptor Antagonist Men 11420 . . . ," Drug Metabolism and Disposition, vol. 26 No. 11 1077-1081, 1998.
Williams et al., "Dicyclomine: worrying symptoms associated with its use in some small babies," British Medical Journal, vol. 288, Mar. 24, 1984, 901.
Wade et al., "Infantile colic," British Medical Journal, Clinical review, vol. 323, Aug. 25, 2001, 437-440.
Metcalf et al., "Simethicone in the Treatment of Infant Colic: A Randomized, Placebo-Controlled, Multicenter Trial," Pediatrics vol. 94 No. 1 Jul. 1994, 29-34.
Danielsson et al., "Treatment of Infantile Colic with Surface Active Substance (Simethicone)," Acta Paediatr Scand 74: 446-450, 1985.
Giuliani et al., "Effect of a tachykinin $NK_2$ receptor antagonist, nepadutant, on cardiovascular and gastrointestinal function in rats and dogs," European Journal of Pharmacology 415 (2001) 61-71.

* cited by examiner

*Primary Examiner*—Julie Ha
(74) *Attorney, Agent, or Firm*—Abelman, Frayne & Schwab

(57) ABSTRACT

Pharmaceutical compositions containing NK2 antagonists are described, useful for the treatment of infantile colics.

7 Claims, No Drawings

PHARMACEUTICAL COMPOSITIONS BASED ON NK2 ANTAGONISTS FOR PEDIATRIC USE

FIELD OF THE INVENTION

The invention relates to pharmaceutical compositions containing an antagonist of tachykinins, specifically neurokinin A, for the treatment of infantile colics.

STATE OF THE ART

The tachykinins are a family of neuropeptides consisting of Substance P (SP) and neurokinins A (NKA) and B (NKB), whose receptors are widely present in the central and peripheral nervous system.

The NKA receptor (NK2) in particular is widely expressed in the peripheral nervous system of mammals. Among the various effects produced by selective stimulation of the NK2 receptor are the modulation of smooth muscle contraction and visceral sensitivity to pain. NK2 antagonists can be considered agents able to control excessive contractions of smooth muscle in any pathological condition, such as irritations or spasms, in which tachykinin release contributes to the development of the disorder. In particular, the bronchospastic component of asthma, cough, pulmonary irritations, intestinal irritations, intestinal spasms, local spasms of the bladder and the ureter during cystitis, kidney infections and colics, can be considered conditions in which the administration of an NK2 antagonist can be effective (A L Magnan et al, Neuropeptides, 1993, 24, 199). Recently, irritable bowel syndrome (IBS) has also been considered as a possible therapeutic target of tachykinin antagonists (M Camilleri, Gastroenterology, 2001, 120, 652). IBS is clinically characterised by chronic abdominal pain associated with disturbed intestinal habits (constipation and/or diarrhoea). The patient with IBS exhibits a reduced sensitivity threshold to visceral pain: this means that low intensity visceral stimuli (e.g. colorectal distension) which are not perceived as painful in the healthy subject are instead perceived as painful and debilitating by the IBS patient (visceral hyperalgesia).

In the past the therapeutic approaches to resolving pain in patients with IBS were aimed at altering intestinal motility by the use of antispasmodic agents, laxatives and prokinetic or anti-diarrhoea agents. Recently visceral hyperalgesia has been recognized as the principle pathophysiological event in IBS symptomology (E A Mayer & F G Gebhart, Gastroenterology, 1994, 107, 271). It has been suggested that drugs able to correct visceral hyperalgesia will constitute an important improvement in IBS treatment.

In animal models, NK2 antagonists have proved capable of reducing visceral hypersensitivity induced by various stimuli (P M Anton et al, Pain, 2001, 92, 219; P G McLean et al, Eur J Pharmacol, 1997, 337, 279).

Various compounds with antagonistic activity towards tachykinins in general and specifically towards NKA have been described in the patent literature over the years. There have also been a number of examples of compounds with the characteristics of NK2/NK3, NK1/NK2 and NK1/NK2/NK3 mixed antagonists.

In WO 93/21227 NK2 antagonists were described with a bicyclic structure; their very low solubility in water has until now prevented any possible pharmaceutical application thereof, despite their interesting in vitro activity.

In EP815126 NK2 antagonists were described with the same bicyclic structure as WO93/21227, but with a hydrophilic part which has rendered them more suitable for pharmaceutical development. One of the molecules described in EP815126, nepadutant, corrects hyperalgesia in animal models of IBS (M Toulouse, Br J Pharmacol, 2000, 129, 193).

In spite of this, the NK2 antagonists described in EP815126 still demonstrate poor oral bioavailability which has rendered this administration route totally unsatisfactory. Nepadutant in particular exhibited very low oral bioavailability (1%) when administered either as a solution to rats (A Lippi et al., Drug Metab Disp, 1998, 26, 1077) or as a dry powder in capsules to human volunteers.

Of the numerous examples of patent literature on this subject, we can cite WO0129066, in which monocyclic NK2 antagonists are described, and WO03037916 with linear NK2 antagonists with basic characteristics.

Infantile colics (IC) are a widely diffuse disorder in infants, whose causes have not been precisely clarified. Excessive crying seems to occur in response to painful intestinal contractions, possibly related to cow's milk allergy, lactose intolerance or flatulence, during physiological maturation of the gastrointestinal tract which could be characterised by a transient increase in intestinal sensitivity. Infantile colics affect both breast fed and artificially fed infants. Despite the favourable and short-term clinical course of infantile colics, this is very stressful for the parents, many of whom seek medical help.

Very few of the drugs commonly proposed and utilized, to varying effect, for adult colics are, or at least are considered to be, potentially usable for treating infantile colics. This is because infantile colics present an etiopathogenesis which cannot be referred back to any adult gastrointestinal disorders, and because of the impossibility of using adult-approved drugs at the pediatric level while at the same time providing guarantees of safety and tolerance. This has discouraged the use of anticholinergic drugs for the therapy of infantile colics, because of the onset of adverse effects (J. Williams et al., British Med. J. 1984, 288: 901), while various attempts at intervention in the infant's diet for therapeutic purposes have not resulted in clinically significant results (S. Wade et al. British Med. J. 2001, 323: 437). The use of drugs which absorb intestinal gas (polysiloxanes, simethicone) has also been questioned due to lack of clinical evidence (the effect appears to be no better than placebo: T J Metcalf et al. Pediatrics, 1994, 94: 29-34; B Danielsson et al., Acta Paediatr. Scand. 1985, 74: 446-50).

In view of the aforesaid differences between adult intestinal disorders and infantile colics the use of tachykinin antagonists, specifically NK2 antagonists or NK2/NK3, NK1/NK2 and NK1/NK2/NK3 mixed antagonists, has hitherto never been postulated for the treatment of these latter.

DETAILED DESCRIPTION OF THE INVENTION

Notwithstanding the lack of definitive conclusions clarifying the causes of infantile colics, it has surprisingly been found that a drug capable of blocking pain symptomology and excessive intestinal motility without altering the basal functions of the infant's intestine can be successfully used in the therapy of infantile colics. In this respect, the activity profile exhibited by tachykinin antagonists, specifically NK2 antagonists or NK2/NK3, NK1/NK2 and NK1/NK2/NK3 mixed antagonists, can be made use of in the preparation of pharmaceutical compositions effective for treating infantile colics.

In infant rats NK2 antagonists have indeed demonstrated the ability, after oral administration, to prevent the increased intestinal transit induced by administration of an NK2 selective agonist, without affecting intestinal basal motility.

The activity demonstrated in infant rats can be used as a predictor of treatment of mammalian infantile colics in general, and in particular of humans.

In EP815126 a series of NK2 antagonists were described, in particular nepadutant, as a potential drug for the treatment of adult pathologies.

It was noted however that these antagonists, including nepadutant, presented the problems of poor bioavailability when administered orally in tests undertaken in both animals and humans.

We have surprisingly found that the bioavailability of these compounds, including nepadutant, was substantially enhanced when formulations containing these active principles were administrated to infant rats, rendering these products particularly suitable for their use in mammalian infantile colics, in which oral administration is the most convenient and simplest implementation.

A preferred group of NK2 antagonists are those described in EP815126, in particular the products of formula (I), more particularly the products included in the group consisting of:
cyclo((Asn(β-D-2-deoxy-2-acetamido-Glc)-Asp-Trp-Phe-Dap-Leu)cyclo(2β-5β)), (nepadutant, example 4),
cyclo((Asn(β-D-galactopyranosyl)-Asp-Trp-Phe-Dap-Leu)cyclo(2β-5β)) (example 12),
cyclo((Asn(4-O-(α-D-Glc)-β-D-Glc)-Asp-Trp-Phe-Dap-Leu)cyclo(2β-5β)) (example 17),
cyclo((Dap(lactobionyl)-Asp-Trp-Phe-Dap-Leu)cyclo(2β-5β)).

A further preferred group of NK2 antagonist compounds in accordance with the present invention is that represented by the compounds described in WO03037916, in particular the products of formula (I) as defined in claims 1-8, more particularly the compounds included in the group consisting of:
N$^\alpha$[N$^\alpha$(benzo[b]thiophenyl-2-ylcarbonyl)-1-aminocyclopentane-1-carbonyl]-D-phenylalanine-N-[3(morpholin-4-yl)propyl]amide (Example 1),
6-Bromo-benzo[b]thiophene-2-carboxylic acid [1-(2-phenyl-1(R)-{[1-(tetrahydro-pyran-4-ylmethyl)-piperidin-4-ylmethyl]-carbamoyl}-ethylcarbamoyl)-cyclopentyl]-amide TFA salt (Example 69),
6-Bromo-naphthalene-2-carboxylic acid [1-(2-phenyl-1(R)-{[1-(tetrahydro-pyran-4-ylmethyl)-piperidin-4-ylmethyl]-carbamoyl}-ethylcarbamoyl)-cyclopentyl]-amide (Example 72),
5-Iodo-benzofuran-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide (Example 127),
6-Methyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide (Example 139), and by the compounds described in WO0129066, in particular the products of formula (I) as defined in claims 1-3, more particularly the compounds included in the group consisting of:
cyclo{-Suc[1-(R)-2(4-morpholin-4-yl piperidin-1-yl)-acetyl amino]-Trp-Phe-[(R)—NH—CH(CH$_2$—C$_6$H$_5$)—CH$_2$NH]—}(example 2),
cyclo{-Suc[1-(R)-2(4-morpholinyl-4-piperidin-1-yl-acetyl)amino]-Trp(5-F)-Phe-[(R)—NH—CH(CH$_2$—C$_6$H$_5$)—CH$_2$NH]—}(example 4).

A further preferred group of compounds for the purposes of the present invention are the NK2 antagonist compounds or the NK2/NK3, NK1/NK2 and NK1/NK2/NK3 mixed antagonist compounds chosen from the group consisting of:

(S)—N-[4-(4-Acetamido-4-phenylpiperidin-1-yl)-2-(3,4-dichlorophenyl)-butyl]-N-methylbenzamide (saredutant, SR48968 by Sanofi-Aventis),
4-[1-[2-[1-(Cyclopropylmethyl)-3(S)-(3,4-dichlorophenyl)-6-oxo-piperidin-3-yl]ethyl]azetidin-3-yl]piperazine-1-sulfonamide (UK224671 by Pfizer),
(+)-(R)—N-[1-[2-[4-Benzoyl-2-(3,4-difluorophenyl)morpholin-2-yl]ethyl]-4-phenylpiperidin-4-yl]-N',N'-dimethylurea (SR144190 by Sanofi-Aventis),
5(S)-(3,4-Dichlorophenyl)-1-(4,4-difluorocyclohexylmethyl)-5-[2-[3-(4-fluoropiperidin-1-yl)azetidin-1-yl]ethyl]piperidin-2-one (UK290795 by Pfizer),
N-[2-(3,4-Dichlorophenyl)-4-[spiro[benzo[b]thiophene-1(3H),4'-piperidin]-1'-yl]butyl]-N-methylbenzamide S-oxide (YM38336 by Yamanouchi),
N-[2-(3,4-Dichlorophenyl)-4-(3-oxo-1,2,3,4-tetrahydrospiro[isoquinoline-1,4'-piperidin]-1'-yl)butyl]-4-fluoro-N-methylbenzamide fumarate (YM44781 by Yamanouchi),
2-Phenyl-3-[4-(1-piperidinyl)piperidin-1-ylmethyl]-N-[1(S),2,2-trimethylpropyl]quinoline-4-carboxamide (SB414240 by GlaxoSmithKline),
2-Benzyl-4-(2-benzyloxyethyl)-1-(N-tert-butylcarbamoyl-L-glutaminyl-L-tryptophyl)semicarbazide (TAC363 by UCB),
5-(3,4-Dichlorophenyl)-4(R)-[N-methyl-3,5-bis(trifluoromethyl)-benzamido]-N-[2-oxoperhydroazepin-3(R)-yl]-2(E)-pentenamide (DNK333 by Novartis),
3-Cyano-N-[2(S)-(3,4-dichlorophenyl)-4-[4-[4-methoxy-2-[[S(S)]-methylsulfinyl]phenyl]piperidin-1-yl]butyl]-N-methylnaphthalene-1-carboxamide citrate (ZD2249 by AstraZeneca),
3-Cyano-N-[2(S)-(3,4-dichlorophenyl)-4-[4-[2-[(S)-methylsulfinyl]phenyl]piperidin-1-yl]butyl]-N-methylnaphthalene-1-carboxamide fumarate (ZD6021 by AstraZeneca),
N-[2-(3,4-Dichlorophenyl)-4-[3-oxo-1,2,3,4-tetrahydrospiro[isoquinoline-1,4'-piperidin]-1'-yl]butyl]-3,4,5-trimethoxy-N-methylbenzamide (YM44778 by Yamanouchi),
1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine] 2(S)-oxide hydrochloride (R113281 by Sankyo),
N-[3(R)-(3,4-Dichlorophenyl)-5-[4-[3(R)-(N-methylcarbamoylmethyl)-2-oxopiperidin-1-yl]piperidin-1-yl]-2(Z)-(methoxyimino)pentyl]-N-methyl-3,5-dichlorobenzamide (SCH206272 by Schering).

Pharmaceutical formulations suitable for treating infantile colics are the oral forms, and in particular:
pediatric drops
syrups.

For preparing the aforesaid pharmaceutical forms of the tachykinin antagonist, and in particular the NK2 antagonist used as an active principle, is present at a concentration from 0.01 to 50 mg/ml, preferably from 0.1 to 10 mg/ml. Said formulations can be used one or more times a day, as required, and based on the advice of the doctor in charge.

Pharmaceutically acceptable excipients for pediatric use are also present, such as sweeteners (sugars, including glucose), flavour enhancers (e.g: fruit flavours, strawberry flavour, raspberry flavour, cream flavour), solubilizing agents (e.g. polysorbate, polyvinylpyrrolidone, carboxymethylcellulose), preservatives and antioxidants (e.g. sorbic acid and ascorbic acid) and others.

These excipients also serve to mask the possible bitter taste of the active principle utilized.

For their administration to the patient, these formulations can be added to foods used for infant feeding, particularly milk.

EXAMPLES

The following are non-limiting examples of the present invention:

Example 1

Formulation in the form of drops for pediatric use containing (per 100 ml of aqueous solution):

| | |
|---|---|
| Nepadutant: | 0.20 g |
| Polysorbate 80 | 1.25 g |
| Glucose | 40 g |
| Sorbic acid | 0.10 g |
| Sodium carboxymethylcellulose | 2.0 g |
| Raspberry flavour | 0.0035 g |
| Cream flavour | 0.0015 g. |

Example 2

Formulation in the form of drops for pediatric use containing (per 100 ml of aqueous solution):

| | |
|---|---|
| Nepadutant: | 0.20 g |
| Polysorbate 80 | 1.25 g |
| Glucose | 25 g |
| Sorbic acid | 0.10 g |
| Sodium carboxymethylcellulose | 2.0 g |
| Raspberry flavour | 0.0035 g |
| Cream flavour | 0.0015 g. |

Example 3

Formulation in the form of drops for pediatric use containing (per 100 ml of aqueous solution):

| | |
|---|---|
| Nepadutant: | 0.20 g |
| Polysorbate 80 | 1.0 g |
| Glucose | 40 g |
| Sorbic acid | 0.10 g |
| Sodium carboxymethylcellulose | 2.0 g |
| Polyvinylpyrrolidone (Povidone F12) | 2.0 g. |

Example 4

Formulation in the form of drops for pediatric use containing (per 100 ml of aqueous solution):

| | |
|---|---|
| Nepadutant: | 0.20 g |
| Polysorbate 80 | 0.5 g |
| Glucose | 40 g |
| Sorbic acid | 0.10 g |
| Hydroxypropyl betadex | 10 g. |

Example 5

Formulation in the form of drops for pediatric use containing:

| | |
|---|---|
| 6-Methyl-benzo[b]thiophene-2-carboxylic acid [1-(2-phenyl-1R-{[1-(tetrahydro-pyran-4-ylmethyl)-piperidin-4-ylmethyl]-carbamoyl}-ethylcarbamoyl)-cyclopentyl]-amide | 10 mg |
| diethylene glycol monoethyl ether | 250 mg |
| polysorbate 20 | 250 mg |
| citric acid | 10 mg. |

Biological Activity

The formulations of the present invention were tested for their biological activity in vivo on newborn rats in accordance with the following method:

a) The NK2 selective agonist β-Ala$^8$-NKA(4-10) was administered intraperitoneally to infant rats aged between 7 and 10 days, both males and females, at a dose of 15 µg/kg. A 10% suspension of carbon in 1% methylcellulose was then administered orally to the animals at a volume of 15 ml/kg. The same carbon-based suspension was administered to a control group which had not received the NK2 agonist.

The administration of β-Ala$^8$-NKA(4-10) at a dose of 15 µg/kg i.p. was found able to produce a significant increase in intestinal transit.

b) A formulation containing nepadutant was administered orally to infant rats aged between 7 and 10 days, both males and females, at doses of 0.5 and 2.5 mg/kg at 2, 4 and 6 hours respectively prior to intraperitoneal administration of the NK2 selective agonist β-Ala$^8$-NKA(4-10) at a dose of 15 µg/kg i.p., selected as the dose able to induce a significant increase in intestinal transit. The administration of Nepadutant proved able to prevent the increase in intestinal transit induced by the stimulation of NK2 receptors by the β-Ala$^8$-NKA(4-10) agonist in a significant manner.

c) In the absence of β-Ala$^8$-NKA(4-10) agonist administration, the administration of formulations containing nepadutant has no effect on basal intestinal transit in infant rats, measured at 6 hours after administration, at a dose of 2.5 mg/kg.

The invention claimed is:

1. A method for treating colic in an infant by administering a pharmaceutical formulation containing a tachykinin antagonist in a pediatric dosage form wherein the tachykinin antagonist is an NK2 antagonist selected from the group consisting of:
   cyclo((Asn(β-D-2-deoxy-2-acetamido-Glc)-Asp-Trp-Phe-Dap-Leu)cyclo(2β-5β)),
   cyclo((Asn(β-D-galactopyranosyl)-Asp-Trp-Phe-Dap-Leu)cyclo(2β-5β)), cyclo((Asn(4-O-(α-DGlc)-β-D-Glc)-Asp-Trp-Phe-Dap-Leu)cyclo(2β-5β)), and cyclo((Dap(lactobionvl)-Asp-Trp-Phe-Dap-Leu)cyclo(2β-5β)).

2. The method according to claim 1 wherein said pharmaceutical formulation is in a form suitable for oral administration.

3. The method according to claim 2 wherein said form is drops.

4. The method according to claim 2 wherein said form is a syrup.

5. The method according to claim 1 wherein the NK2 antagonist is cyclo((Asn (β-D-2-deoxy-2-acetamido-Glc)-Asp-Trp-Phe-Dap-Leu)cyclo(2β-5β)).

6. The method according to claim 1 wherein the tachykinin antagonist is present in a concentration from 0.01 to 50 mg/ml.

7. The method according to claim 1 wherein the tachykinin antagonist is present in a concentration from 0.1 to 10 mg/ml.

* * * * *